ABSTRACT

Compounds having the formula

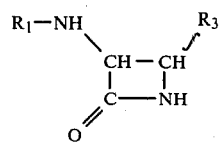

can be prepared by reacting a compound having the formula

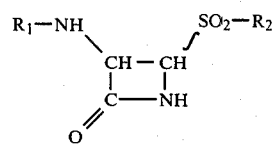

with a Grignard reagent having the formula

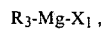

wherein $R_1$ is phenylacetyl or phenoxyacetyl;
$R_2$ is a not readily enolyzable alkyl group, aryl or norbornyl;
$R_3$ is alkyl, alken-1-yl, alkyn-1-yl, 2-phenylethenyl, 2-phenylethynyl, aryl or arylalkyl;
$X_1$ is bromine or chlorine.

(3R-cis)-3-Acylamino-4-norbornylsulfonyl-2-azetidinones are novel compounds that form an integral part of this invention.

2 Claims, No Drawings

United States Patent [19]

Mueller et al.

[11] 4,421,686

[45] Dec. 20, 1983

[54] 4-NORBORNYL-SULFONYL AZETIDINONE INTERMEDIATES AND PROCESS FOR PREPARING (S)-3-ACYLAMINO-4-SUBSTITUTED-2-AZETIDINONES

[75] Inventors: Richard H. Mueller, Lawrenceville; Christopher M. Cimarusti, Pennington; Thomas P. Kissick, Princeton, all of N.J.

[73] Assignee: E. R. Squibb & Sons, Inc., Princeton, N.J.

[21] Appl. No.: 416,837

[22] Filed: Sep. 13, 1982

Related U.S. Application Data

[62] Division of Ser. No. 325,781, Nov. 30, 1981.

[51] Int. Cl.³ ............................................. C07D 205/08
[52] U.S. Cl. ................................................. 260/239 A
[58] Field of Search ..................................... 260/239 A

[56] References Cited

FOREIGN PATENT DOCUMENTS 2071650 9/1981 United Kingdom .

OTHER PUBLICATIONS

J. C. S. Chem. Comm., 1980, 736–737.
J. Chem. Soc., Perkin Trans. I, 1187 (1973).

Primary Examiner—Mark L. Berch
Attorney, Agent, or Firm—Lawrence S. Levinson; Donald J. Barrack

4-NORBORNYL-SULFONYL AZETIDINONE INTERMEDIATES AND PROCESS FOR PREPARING (S)-3-ACYLAMINO-4-SUBSTITUTED-2-AZETIDINONES

This is a division of application Ser. No. 325,781, filed Nov. 30, 1981.

RELATED APPLICATION

U.S. patent application Ser. No. 226,562, filed Jan. 19, 1981 describes (S)-3-acylamino-2-oxo-1-azetidinesulfonic acids having various substituents in the 4-position. One of the processes described by this application utilizes a starting material having the formula

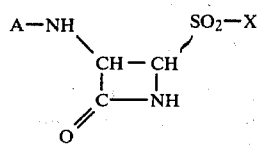

wherein A is a nitrogen protecting group (triphenylmethyl is said to be preferred) and X is alkyl or phenyl. As disclosed therein, a compound of the above formula can be reacted with one (1) equivalent of a methyl Grignard reagent followed by slightly more than one (1) equivalent of the appropriate Grignard reagent having the formula

halo-Mg-R wherein R is alkyl, alken-1-yl, alkyn-1-yl, 2-phenylethenyl or 2-phenylethynyl to yield a compound having the formula

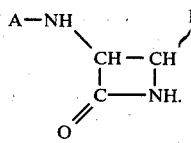

BACKGROUND OF THE INVENTION

"A New Method for the Carbon-extension Reactions of Azetidin-2-ones", Kobayashi et al., J.C.S. Chem. Comm., 1980, 736-737, describes treatment of 4-sulfonylazetidin-2-ones and 3-triphenylmethyl-4-sulfonylazetidin-2-ones with Grignard reagent. Specifically utilized as starting materials are 4-phenylsulfonylazetidin-2-one and 3-triphenylmethyl-4-methylsulfonylazetidin-2-one.

U.K. Patent Application No. 2,071,650, published Sept. 23, 1981, describes (S)-3-acylamino-2-oxo-1-azetidinesulfonic acids having various substituents in the 4-position, and the use of these compounds as antibacterial agents.

"Transformations of Penicillins. Part V. Reactions of Olefin and Acetylene Derivatives with the Sulphenic Acid Intermediates from Penicillin S-Oxides", Ager et al., J. Chem. Soc., Perkin Trans. I, 1187 (1973), describes the trapping reaction of, inter alia, norbornadiene with the sulphenic acids produced by heating penicillin S-oxides followed by reduction to yield

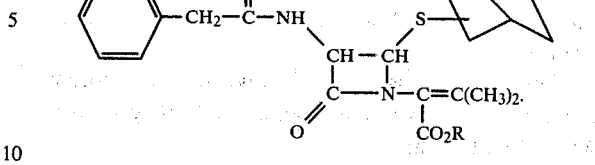

Brief Description of the Invention

While the prior art deals with carbon-extension reactions of 3-unsubstituted and 3-protected amino azetidin-2-ones, it has now been surprisingly found that compounds having the formula

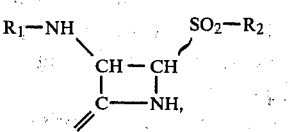

wherein $R_1$ is one of the simple acyl groups phenylacetyl or phenoxyacetyl, can be treated with a Grignard reagent having the formula

$$R_3-Mg-X,\quad \text{II}$$

to yield the corresponding compounds having the formulas

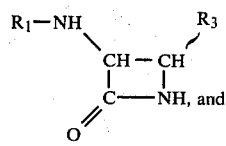

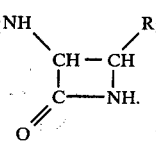

In the above formulas, and throughout the specification, the symbols are as defined below.

$R_1$ is phenylacetyl or phenoxyacetyl;

$R_2$ is a not readily enolizable alkyl group, aryl or norbornyl;

$R_3$ is alkyl, alken-1-yl, alkyn-1-yl, 2-phenylethenyl, 2-phenylethynyl, aryl or arylalkyl; and $X_1$ is bromine or chlorine, preferably chlorine.

Listed below are definitions of various terms used herein. These definitions apply to the terms as they are used throughout the specification (unless they are otherwise limited in specific instances) either individually or as part of a larger group.

The term "alkyl" refers to both straight and branched chain groups. Those groups having 1 to 10 carbon atoms are preferred.

The term "aryl" refers to phenyl or phenyl substituted with 1, 2 or 3 alkyl (of 1 to 4 carbon atoms) or alkoxy (of 1 to 4 carbon atoms) groups.

The terms "alken-1-yl[ and "alkyn-1-yl" refer to both straight and branched chain groups. Those groups having 2 to 10 carbon atoms are preferred.

The term "a not readily enolizable alkyl group" refers to groups that enolize at a rate slower than the rate of the substitution reaction of this invention. Exemplary of such groups are the branched chain alkyl groups such as isopropyl and t-butyl.

Those compounds of formula I wherein $R_2$ is norbornyl are novel compounds, and as such, they form an integral part of this invention.

DETAILED DESCRIPTION OF THE INVENTION

The discovery that the prior art processes discussed above can be modified to utilize starting materials of formula I is of great significance. Compounds of formula I are obtained from the well known fermentation products penicillin G (benzyl penicillin), penicillin V, or 6-APA(6-aminopenicillanic acid), using any one of several reaction sequences.

One such reaction sequence comprises conversion of pen G or pen V to the corresponding sulfoxide ester (see, for example, *Cephalosporins and Penicillins, Chemistry and Biology*, E. H. Flynn, editor., Academic Press, 1972), followed by rearrangement, in-situ norbornylene trapping and conjugation to give a compound having the formula

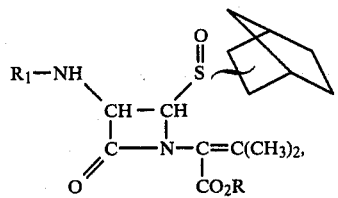

wherein the "$CO_2R$" group is an esterified carboxyl group, such as an alkyl ester or trialkylsilyl ester. Subsequent oxidation and cleavage by treatment with an acid yields the corresponding (3R-cis)-3-acylamino-4-norbornylsulfonyl-2-azetidinone having the formula

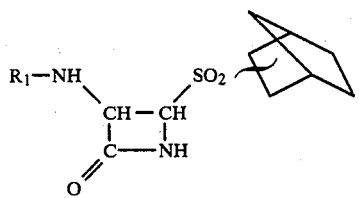

as a mixture of diastereomers. The mixture can be separated using conventional techniques or preferably, will be used in the next step of the process of this invention as a mixture. Compounds of formula V form an integral part of this invention.

Treatment of the above (3R-cis)-3-acylamino-4-norbornylsulfonyl-2-azetidinone with the appropriate mercaptan having the formula $R_2$-SH in the presence of a base yields the corresponding compound having the formula

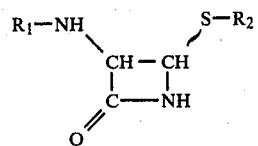

(see *J. Org. Chem.*, 38:940 (1973)), which can be oxidized to yield the desired starting material of formula I.

Alternatively, pen G or pen V can be converted to 6-APA, which can be converted to a compound having the formula

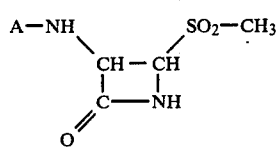

(see *J. Chem. Soc.*, Perkin I, 562 (1975)). Treatment of a compound of formula VII with sodium aryl sulfinate in the presence of tetra-n-butyl ammonium bromide under phase transfer conditions gives the corresponding compound having the formula

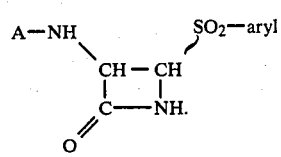

Deprotection of a compound of formula VIII followed by acylation yields the desired starting material of formula I (wherein $R_2$ is aryl) as a mixture of the cis and trans isomers, which are separable by fractional crystallization and/or column chromatography.

The conversion of a compound of formula I to a mixture of compounds of formulas IIIa and IIIb is accomplished by treating a compound of formula I with a Grignard reagent of formula II, preferably in the presence of a Lewis acid. Magnesium chloride is the preferred Lewis acid. The conversion is accomplished most efficiently using an excess of Grignard reagent, preferably three (3) molar equivalents, and most preferably, four (4) or five (5) molar equivalents. Preferably about four (4) to six (6) molar equivalents of Lewis acid are used.

A mixture of compounds of formulas IIIa and IIIb can be separated using art-recognized techniques such as column chromatography and fractional crystallization.

The compounds of formulas IIIa and IIIb can be converted to the corresponding compound having the formula

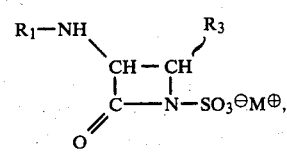

wherein $M^\oplus$ is hydrogen or a cation, using the procedures described in U.K. patent application 2,071,650. As described therein, a sulfo substituent ($-SO_3^\ominus M^\oplus$) can be added to the 1-position of an azetidin-2-one by treatment of the azetidin-2-one with a complex of pyridine, 2,6-lutidine or dimethylformamide and sulfur trioxide. An alternative procedure described by the United Kingdom patent comprises silylating an azetidin-2-one (unsubstituted in the 1-position) and then subjecting the silated compound to a silyl interchange reaction. Exemplary silylating agents are monosilyltrifluoroacetamide, trimethylsilylchloride/triethylamine, and bis-trimethylsilyltrifluoroacetamide, and an exemplary reagent useful for the silyl interchange reaction is trimethylsilyl chlorosulfonate.

A compound of formula IX can be converted to the corresponding compound having the formula

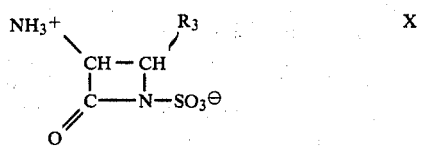

by treatment with phosgene followed by treatment with methanol and acid.

Using conventional acylation techniques, a compound of formula X can be converted to the corresponding compound having the formula

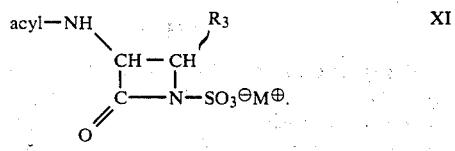

As described in U.K. patent application No. 2,071,650, a compound of formula X can be reacted with a carboxylic acid, or corresponding carboxylic acid halide or anhydride. The reaction with a carboxylic acid proceeds most readily in the presence of a carbodiimide such as dicyclohexylcarbodiimide and a substance capable of forming an active ester in situ such as N-hydroxybenzotriazole. In those instances when the acyl group contains reactive functionality (such as amino or carboxyl groups) it may be necessary to first protect those fuunctional groups, then carry out the acylation reaction, and finally deprotect the resulting product.

The β-lactam antibiotics of formula XI can be used as agents to combat bacterial infections (including urinary tract infections and respiratory infections) in mammalian species, such as domesticated animals and humans. The prior art discloses that for combating bacterial infections in mammals a compound of formula XI can be administered to a mammal in need thereof in an amount of about 1.4 mg/kg/day to about 350 mg/kg/day, preferably about 14 mg/kg/day to about 100 mg/kg/day.

The following examples are specific embodiments of this invention.

Preparation of Starting Materials (3R-cis)-3-Phenylacetylamino-4-norbornylsulfonyl-2-azetidinone (A) Penicillin G Sulfoxide Penicillin G, potassium salt (349.9 g) was dissolved in 3 liters of water. Sodium periodate (194 g) was added and the mixture was stirred for three hours. Dichloromethane (500 ml) was added and the pH of the water layer was adjusted to 2.3 with 6 N hydrochloric acid with vigorous stirring. The aqueous layer was separated and extracted with four 400 ml portions of dichloromethane. The combined extract was washed with aqueous sodium bisulfite to remove any iodine color, dried over sodium sulfate, filtered, and evaporated. The solid residue was empasted with 400 ml of ethyl acetate and allowed to stand at 0° C. overnight. The solid was isolated by filtration and dried in vacuo to afford 322 g of penicillin G sulfoxide.

(B) Penicillin G Sulfoxide, methyl ester

Penicillin G sulfoxide (321.9 g) and 1000 ml of dichloromethane were cooled in an ice/water bath. A solution of 139.7 g dicyclohexylcarbodiimide in 50 ml of dichloromethane was added followed by a solution of 1.5 g of dimethylaminopyridine in 80 ml of anhydrous methanol. The cold bath was removed and the mixture was stirred for 3.5 hours. The dicyclohexylurea was removed by filtration and 1000 ml of ethyl acetate was added to the filtrate. The organic layer was washed with sodium bicarbonate solution, water, aqueous sodium dihydrogen phosphate, and water, then dried over sodium sulfate. The solvent was evaporated and the residue was slurried with ethyl acetate to afford 149.6 g of the methyl ester of penicillin G sulfoxide.

(C) (3R-cis)-3-Phenylacetylamino-4-norbornylsulfonyl-2-azetidinone

Finely ground penicillin G sulfoxide methyl ester (25 g) was added in small portions to 250 ml of hot norbornylene containing 6 ml of dioxane. The mixture was refluxed for 16 hours, then most of the excess norbornylene was removed by distillation at 1 atmosphere. Toluene (200 ml) was added and the mixture was evaporated in vacuo. The residue was dissolved in 50 ml of dichloromethane and 50 ml of triethylamine was added. After 30 minutes, the mixture was evaporated and chased with toluene. The resulting dark oil was dissolved in 300 ml of dimethylformamide, 80 ml of acetic acid, and 50 ml of water in a 2000 ml flask equipped with a mechanical stirrer. Powdered potassium permanganate (40 g) was added in portions over 20 minutes with cooling in an ice/acetone bath (the temperature was maintained below −5° C.). After another 40 minutes 500 ml of ethyl acetate and 500 ml of water were added. Sodium sulfite was added slowly until all of the brown manganese dioxide was dissolved. Additional ethyl acetate was added and the organic phase was washed four times with water, then with sodium bicarbonate solution, and then with saturated brine. The organic layer was dried over sodium sulfate, the ethyl acetate was evaporated and the residue was crystallized from 20 ml of chloroform plus 150 ml of diethyl ether to give 8.2 g of (3R-cis)-3-phenylacetylamino-4-norbornylsulfonyl-2-azetidinone.

(3R-cis and trans)-3-Phenoxyacetylamino-4-phenylsulfonyl-2-azetidinone (A) (3R-cis and trans)-3-Triphenylmethyl-4-phenylsulfonyl-2-azetidinone A mixture of 30 g of (3R-cis)-3-triphenylmethyl-4-methylsulfonyl-2-azetidinone, 40 g of sodium benzenesulfinate, 25 g of tetra-n-butylammonium bromide, 400 ml of 1,2-dichloroethane, and 100 ml of water were refluxed under nitrogen for 30 minutes. The dichloroethane was removed in vacuo and the residue was extracted with 700 ml of ethyl acetate. The extract was washed with saturated aqueous sodium bicarbonate solution, then water, then saturated aqueous sodium chloride solution. The extract was dried over sodium sulfate and evaporated. The residue was chromatographed on a 50×280 mm silica gel column eluted with 1000 ml 1:4 ethyl acetate:hexane, then 1000 ml 1:1 ethyl acetate:hexane. (3R)-3-triphenylmethyl-4-phenylsulfonyl-2-azetidinone (25.3 g) was obtained as a mixture of cis and trans isomers.

(B) (3R-cis and trans)-3-Amino-4-phenylsulfonyl-2-azetidinone,hydrochloride (3R-cis and trans)-3-triphenylmethyl-4-phenylsulfonyl-2-azetidinone (20.3 g) was dissolved in 200 ml of acetone. Hydrochloric acid (7.2 ml, 12 N) was added with stirring. After 2.5 hours, the resulting solid was isolated by filtration, washed with acetone, and dried in vacuo to afford 7.6 g of (3R-cis and trans)-3-amino-4-phenylsulfonyl-2-azetidinone, hydrochloride.

(C) (3R-cis and trans)-3-Phenoxyacetylamino-4-phenylsulfonyl-2-azetidinone

To an ice-cooled mixture of 7.6 g of 3-amino-4-phenylsulfonyl-2-azetidinone (mixture of cis and trans isomers), 5.1 g of sodium bicarbonate 100 ml of dichloromethane, and 50 ml of water was added dropwise with vigorous stirring 4.0 ml phenoxyacetyl chloride. After 90 minutes the resulting solid was removed by filtration and washed with water and dichloromethane. The solid was dissolved in tetrahydrofuran and precipitated with toluene to give 3.85 g of (3R-trans)-3-phenoxyacetylamino-4-phenylsulfonyl-2-azetidinone, melting point 192°–193° C., dec.

The reaction mixture filtrate was diluted with dichloromethane, washed with water, dried over sodium sulfate, and evaporated to give 4.7 g of a residue which contained both cis and trans isomers. The residue was triturated with 150 ml of hot chloroform, let stand for 2 hours at 25° C., and then filtered to give 1.2 g of the trans isomer. The mother liquor was evaporated and taken up in hot methanol from which 1.35 g of (3R-cis)-3-phenoxyacetylamino-4-phenylsulfonyl-2-azetidinone, melting point 178°–180° C. (dec), crystallized.

(3R-cis and trans)-3-Phenylacetylamino-4-phenylsulfonyl-2-azetidinone

The title compound is prepared using the procedure described above for the preparation of the analogous 3-phenoxyacetylamino compound; phenylacetyl chloride is substituted for phenoxyacetyl chloride in part C of the procedure.

(3R-cis)-3-Phenoxyacetylamino-4-norbornylsulfonyl-2-azetidinone

The title compound is prepared using the procedure described above for the preparation of the analogous 3-phenylacetylamino compound; penicillin V, potassium salt is substituted for penicillin G, potassium salt in part A of the procedure.

Processes for Preparing
(S)-3-Acylamino-4-Substituted-2-Azetidinones (cis) and
(trans)-3-Phenoxyacetylamino-4-methyl-2-azetidinone Methyl magnesium chloride (2.9 ml, of 2.9 M in tetrahydrofuran) was added to a solution of 500 mg (3R-trans)-3-phenoxyacetylamino-4-phenylsulfonyl-2-azetidinone in 11.1 ml of 0.5 M magnesium dichloride in tetrahydrofuran under nitrogen and chilled in an ice-/acetone bath (−10° C.). After 2 hours, the mixture was added to saturated aqueous ammonium chloride and extracted with ethyl acetate. The extract was washed with water, dried over sodium sulfate, and evaporated. Treatment of the residue with dichloromethane/ethyl ether gave 106 mg of cis-3-phenoxyacetylamino-4-methyl-2-azetidinone. The corresponding trans isomer, as well as some cis isomer, was present in the mother liquor, as shown by NMR.

(cis) and
(trans)-3-Phenylacetylamino-4-methyl-2-azetidinone

METHOD I

To 500 mg (3R-trans)-3-phenylacetylamino-4-phenylsulfonyl-2-azetidinone in 20 ml tetrahydrofuran under nitrogen and cooled in ice/acetone (−18° C.) was added 2.5 ml of 2.9 M methyl magnesium chloride in tetrahydrofuran. After 3.5 hours, the bath temperature had risen to −5° C.; the reaction mixture was then added to saturated aqueous ammonium chloride. The mixture was extracted twice with dichloromethane. The combined extract was dried over sodium sulfate, filtered, and evaporated in vacuo to give 300 mg residue. NMR indicated an approximate ratio of 15:85 trans:cis-3-phenylacetyl-4-methyl-2-azetidinone. The product was dissolved in 2 ml chloroform and precipitated with 3 ml ethyl ether to give 184 mg cis-3-phenylacetylamino-4-methyl-2-azetidinone.

METHOD II

Methyl magnesium chloride (3.0 ml of 2.9 M in tetrahydrofuran) was added to 500 mg (3R-trans)-phenylacetylamino-4-phenylsulfonyl-2-azetidinone dissolved in 11.6 ml of 0.5 M magnesium chloride in tetrahydrofuran under nitrogen and chilled in an ice/acetone bath to −10° C.; the reaction mixture was poured into saturated aqueous ammonium chloride. The mixture was extracted with ethyl acetate. The extract was washed with water, dried over sodium sulfate, and evaporated. The residue was treated with dichloromethane/ethyl ether to afford 126 mg cis-3-phenylacetylamino-4-methyl-2-azetidinone. As shown by NMR, the mother liquor contained the corresponding trans isomer as well as some cis isomer.

METHOD III

A solution of methylmagnesium chloride (2.9 M in tetrahydrofuran, 2.2 ml, 6.36 mM) was added to 384 1 mg (1.06 mM) (3R-cis-3-phenylacetylamino-4-norbornylsulfonyl-2-azetidinone dissolved in 8.5 ml of 0.5 M magnesium chloride in tetrahydrofuran (prepared by the reaction of 2 ml, 1,2-dichloroethane with 0.73 g magnesium in 50 ml of tetrahydrofuran) at 0° C. in an ice water bath. The bath was allowed to warm to room temperature over 90 minutes. After another 60 minutes, the reaction mixture was poured into saturated aqueous ammonium chloride. The mixture was extracted with ethyl acetate; the extract was washed with water, dried, and evaporated. The residue was chromatographed on a silica gel column with ethyl acetate/hexane, to afford 3-phenylacetylamino-4-methyl-2-azetidinone as a 1:2 mixture of cis and trans isomers, respectively.

(cis) and
(trans)-3-Phenylacetylamino-4-ethyl-2-azetidinone

To 420 mg (3R-trans)-3-phenylacetylamino-4-phenylsulfonyl-2-azetidinone in 20 ml tetrahydrofuran under nitrogen and cooled in an ice/acetone bath to −10° C.

was added 3.8 ml of 2.08 M ethyl magnesium chloride in tetrahydrofuran. After 4.5 hours, the bath temperature had risen to 0° C.; the mixture was added to saturated aqueous ammonium chloride and extracted twice with dichloromethane. The combined extract was washed with water, dried over sodium sulfate, filtered and evaporated. The residue was chromatographed on a silica gel column eluted with 40% ethyl acetate in dichloromethane to give 103 mg product as a cis and trans mixture of 3-phenylacetylamino-4-ethyl-2-azetidinone in an approximate 5:2 cis:trans ratio.

What is claimed is:
1. (3R-cis)-3-Phenylacetylamino-4-norbornylsulfonyl-2-azetidinone.
2. (3R-cis)-3-Phenoxyacetylamino-4-norbornylsulfonyl-2-azetidinone.

* * * * *